United States Patent [19]

Lindsay-Scott et al.

[11] Patent Number: 4,791,922
[45] Date of Patent: Dec. 20, 1988

[54] GAS FLOW CONTROL APPARATUS FOR AN ANAESTHESIA SYSTEM

[75] Inventors: David Lindsay-Scott, Lodeve, France; Malcolm K. Sykes, Iffley, England; Basil R. Sugg, Oxford, England; Paul J. Tyrrell, Oxon, England

[73] Assignee: Penlon Limited, Abingdon, United Kingdom

[21] Appl. No.: 2,618
[22] PCT Filed: Apr. 11, 1986
[86] PCT No.: PCT/GB86/00206
§ 371 Date: Feb. 11, 1987
§ 102(e) Date: Feb. 11, 1987
[87] PCT Pub. No.: WO86/05992
PCT Pub. Date: Oct. 23, 1986

[30] Foreign Application Priority Data

Apr. 12, 1985 [GB] United Kingdom ............... 8509413

[51] Int. Cl.[4] .................................................. A62B 7/10
[52] U.S. Cl. .................................................. 128/205.28
[58] Field of Search .................. 128/204.28, 205.28, 128/203.28, 205.12, 205.24, 205.27

[56] References Cited

U.S. PATENT DOCUMENTS 3,046,979 10/1965 Andreasen ............... 128/205.15
4,351,329 9/1982 Ellestad et al. ............ 128/205.24

Primary Examiner—Francis Jaworski
Assistant Examiner—George Manuel
Attorney, Agent, or Firm—Foley & Lardner, Schwartz, Jeffery, Schwaab, Mack, Blumenthal & Evans

[57] ABSTRACT

An apparatus for controlling the flow of gas to and from a patient in an anaesthesia system has first and second flow passages arranged in parallel between the patient and a reservoir bag. Selector valves allow multiple anaesthesia configurations involving no rebreathing or considerable rebreathing. A selector valve can be operated to connect the reservoir bag to either or both flow passages. A one way valve in the first passage, which communicates with a gas supply inlet, can be operated to prevent the back flow of gas from the patient into the passage. A one way valve in the second passage can selectively prevent the flow of gas in the second passage to the patient. The second passage has a selectively bypassable carbon dioxide absorbing fitter and a spill valve. The apparatus allows reconfiguration without disconnecting and reconnecting hoses.

11 Claims, 10 Drawing Sheets

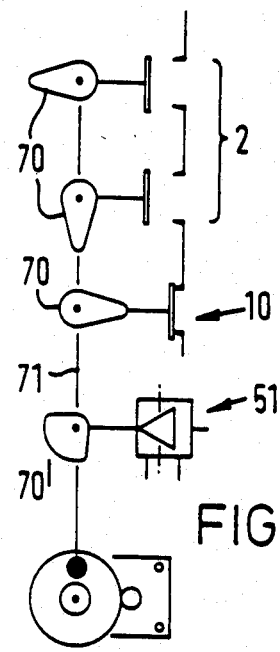
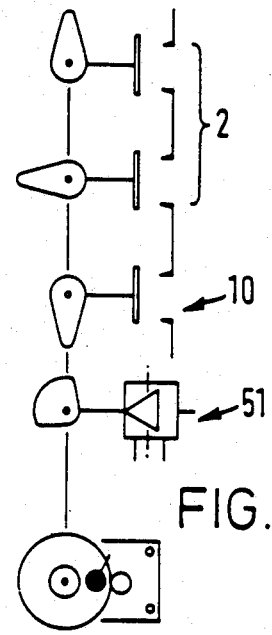
FIG.13a       FIG.13b
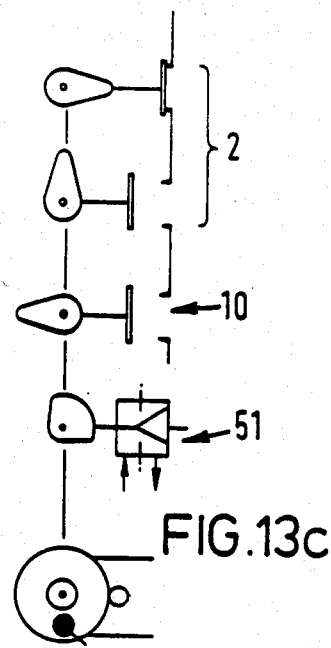
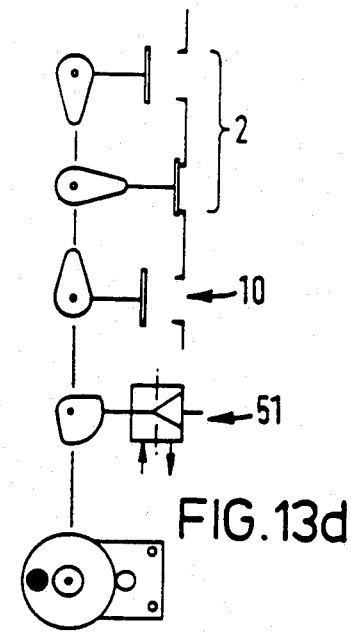
FIG.13c       FIG.13d

GAS FLOW CONTROL APPARATUS FOR AN ANAESTHESIA SYSTEM

This invention relates to apparatus for controlling the flow of gas to and from a patient in an anaesthesia system, and relates in particular to such apparatus whereby any one of several gas supply circuits may be selected without the need to change the connecting lines extending between the apparatus and the patient.

In present day anaesthetic practice there are many different systems for the supply of anaesthetic gases to and from a patient, each having particular characteristics relating to the gas flow to the patient from an anaesthesia machine and to the expiratory flow from the patient. In certain of these systems the patient may either breathe spontaneously, or, alternatively, mechanical ventilation may be provided, while other systems may only be used satisfactorily with one or the other mode of breathing. In addition, some systems cause the patient to rebreathe a portion of his expired gases, while in other systems there is little or no rebreathing and the only the fresh gas supplied by the anaesthesia machine enters the patient's lungs.

Commonly used gas supply systems which are familiar to those skilled in the art include the Mapleson A and Mapleson D systems. The former while allowing little to no rebreathing is generally suitable only for a patient who breathes spontaneously, and the latter, which does allow rebreathing, may be used with a spontaneously breathing patient or where a mechanical lung ventilator is required. Other systems which may be applicable depending on particular clinical conditions, include the so-called circle system where expired gases are passed through a carbon dioxide absorbing means before being returned to the patient.

In the conventional anaesthesia apparatus, when it is desired to switch from one gas supply system to another, it has generally been necessary to disconnect and reconnect hoses or pipes in the apparatus in accordance with the particular gas supply system required. This process is time consuming and inconvenient to the physician, and considerable care and attention must be given to ensure that the correct connections are made so that undesirable and potentially dangerous configurations are avoided.

In accordance with the invention there is provided apparatus for controlling the flow of gas to or from a patient in an anaesthesia system. The apparatus has a reservoir bag, and a selector valve means operable to connect the reservoir bag to either or both of first and second flow passages. The passages are arranged in parallel and adapted to be connected to a patient at on end remote from the selector valve means. The first passage has a first one-way valve means selectively operable to prevent the back-flow of gas from the patient into the passage. The first passage communicates with an inlet for the supply of fresh gas. A second flow passage has a second one-way valve means selectively operable to prevent the flow of gas from the passage to the patient and a selectively bypassable carbon dioxide absorbing means, there being a spill valve arranged to release gases from the second flow passage. Means are provided to control the conditions of the selector valve means and first and second one-way valve means whereby desired modes of operation of the apparatus may be selected.

The fresh gas supplied to the first flow passage via the inlet will depend on clinical conditions and may, for example, consist of a mixture of oxygen, nitrous oxide and anaesthetic vapour. As in conventional anaesthesia systems a number of different gases may be used.

In accordance with the invention, various modes of operation, corresponding to a number of different traditional gas supply systems, may be selected without the need manually to disconnect and reconnect hoses forming part of the apparatus or those extending between the apparatus and the patient. At the same time, the arrangement may be such that undesirable and potentially dangerous modes of operation are avoided. This is very important if safety standards are to be maintained.

In a first mode of operation, the selector valve means is actuated so that the reservoir bag is connected to the first flow passage while the flow of gas between the second flow passage and the bag is prevented. In this mode both one-way valves are retained in an inoperative condition in which they allow flow in each direction. and The carbon dioxide absorbing means in the second flow passage, for example a filter containing soda-lime in granular form, is bypassed. Those skilled in the art will recognize this mode of operation of the apparatus as being equivalent to a Mapleson A gas supply system, which is particularly suited for use with a patient who breathes spontaneously.

A second mode of operation corresponds to a Mapleson D system. In this mode the selector valve means is actuated such that the reservoir bag is connected to the second flow passage and is shut off from the first. This mode promotes a considerable degree of rebreathing, since the fresh gas is supplied via the first passage which is shut off from the reservoir bag and thus forms a low compliance line.

The third mode of operation corresponds to a circle system which again promotes a considerable degree of rebreathing. In this mode, the selector valve means is actuated such that the reservoir bag is connected to both the first and the second flow passages. In addition, the one-way valve means are operated such that gas may only be supplied to the patient via the first flow passage, and expired gases may only leave the patient via the second passage. In this mode gases are effectively recirculated to and from the patient via the first and second passages, compliance being provided by the ventilation bag. Generally, in this mode the soda-lime filter will not be bypassed since carbon dioxide needs to be removed from the expired gases before these are recirculated to the patient.

A fourth mode of operation allows no rebreathing whatsoever. In this mode, the one-way valve means are again operated, and the selector valve means is actuated such that the ventilator bag is connected to the first flow passage and shut off from the second.

In a final mode, the fresh gas supply may be isolated such that a common gas outlet configuration is provided to which any conventional type of anaesthetic breathing system may be attached if it is not desired to use one of the preferred modes discussed above. In such a configuration the one-way valve means remain inoperative.

In all the above modes of operation, excess gas may be vented from the apparatus via the spill valve communicating with the second flow passage as the patient exhales. As is conventional, the spill valve could comprise a non-return valve adapted to prevent air entering the system.

With the exception of the Mapleson A and common gas outlet configurations, each of the above modes of operation are suitable for use in controlled, mechanical ventilation as well as for use with a reservoir bag where a patient breathes spontaneously. Thus, in a preferred embodiment, the apparatus also has a mechanical ventilator and switching valve means which can be actuated to connect either the mechanical ventilator or the reservoir bag to the selector valve means. Thus, in this embodiment, either an automatic mode, wherein the mechanical ventilator is actuated and is connected to the selector valve means or a spontaneous breathing mode wherein the reservoir bag is connected to the selector valve means, may be selected. In the latter mode, as with conventional systems, breathing may be promoted manually by the physician squeezing the reservoir bag, if necessary.

Where mechanical or hand controlled ventilation is used, it is important that during inflation of the patient's lungs gases cannot escape from the apparatus via the one-way spill valve. Therefore, it is means preferable to provide for preventing opening of the spill valve in synchronism with inhalation during mechanical or hand controlled ventilation.

In a preferred embodiment, the mechanical ventilator is a compressible bellows mounted within a rigid, which chamber can be pressurized and opened to atmosphere in a cyclical manner by, for example, an electronically controlled valve. The chamber is pressurized by a drive gas and, when pressurized, the bellows are compressed, forcing the anaesthetic gases into the lungs of the patient. When the chamber is opened to atmosphere, the relaxation of the patient's chest and lungs will cause the gas to flow from the lungs back into the bellows. In this embodiment, the sealing of the spill valve during inflation may be achieved by means of a pressure sensitive closure member of the spill valve in flow communication with the drive gas inlet of the mechanical ventilator. Similarly, where hand controlled ventilation is used by the physician, the closure member is in flow communication with the outlet from the reservoir bag, such that, when the bag is compressed by the physician, the resulting increase in pressure causes the spill valve to be closed.

The structure of the various valve means and the nature of the means for controlling the conditions of various valve means in accordance with the invention may vary. In one embodiment the apparatus is monitored and controlled by a suitable electronic control means and the various valve means are individually actuable in response to control signals from the control means. The control means is programmed to select the desired operational configuration discussed above and to avoid unwanted, potentially dangerous modes. In such an embodiment, the valves may conveniently comprise solenoid controlled valves.

In an alternative embodiment, a mechanical actuating means may be provided for certain of the valve means. In one such embodiment, the selector valve means comprises cam operated poppet valves, the valve closure members of which are operated by cams carried by a rotatable shaft. Rotation of the shaft thus is effective to change the setting of the selector valve means. In such an arrangement, a valve arranged to control whether or not the carbon dioxide absorbing means is bypassed may likewise conveniently comprise a poppet valve operable by a futher cam carried by the rotatable shaft. The shaft may be rotated either manually or by an electric motor responsive, to electronic control means of the apparatus. Preferably, suitable sensing means are provided, such that the control means may monitor the angular position of the shaft and thus the condition of the valve means.

In a preferred embodiment, the one-way valve means in the first and second flow passages comprise gravity operated disc valves. In one embodiment, such valves are rendered inoperable simply by being selectively bypassed when not required. In a preferred embodiment, however, each valve may be made operable or inoperable by the lowering or raising of a pin or rod arranged to extend through the valve seat. In the raised condition the valve closure member is prevented from seating that gases can flow either way through the valve. Such valves may conveniently be pneumatically operable. In a preferred embodiment the actuating pressure signals are controlled by a further cam actuated poppet valve mounted on a common unit with the preferred selector valve and carbon dioxide absorber bypass valve discussed above.

It is desirable that the selector valve means and the one way valve means be constructed so that in the event of a power failure the apparatus will remain in a selected mode. It will be appreciated that this will be so in the case of the preferred cam actuated poppet valves discussed above. By contrast, in those embodiments comprising a mechanical ventilator, the switching valve which selects either the mechanical ventilator or the ventilator bag is preferably biased so that, in the event of either power failure or gas supply failure, the valve resumes a position wherein the bag is connected to the patient to permit spontaneous breathing or manual ventilation. In a preferred such embodiment, the switching valve is operated by gas pressure, under the control of an electrically operable solenoid valve, so that both the electricity and gas supplies must be provided to switch the valve to the mechanical ventilation mode.

In a preferred embodiment, electronic control means for the apparatus forms part of a central microprocessor adapted automatically to control and monitor other aspects of an anaesthesia system. As mentioned above, means may be provided to sense and provide a signal indicative of the condition of the various valve means, such that the control means may monitor whether or not the apparatus is functioning correctly and has adopted the selected mode. A suitable alarm signal may be given in the event of a valve failure.

Certain embodiments of the invention will now be described, by way of example only, with reference to the accompanying drawings, wherein:

FIGS. 13a to 13d illustrate schematically the operational configurations of the valve unit.

Figure 1:
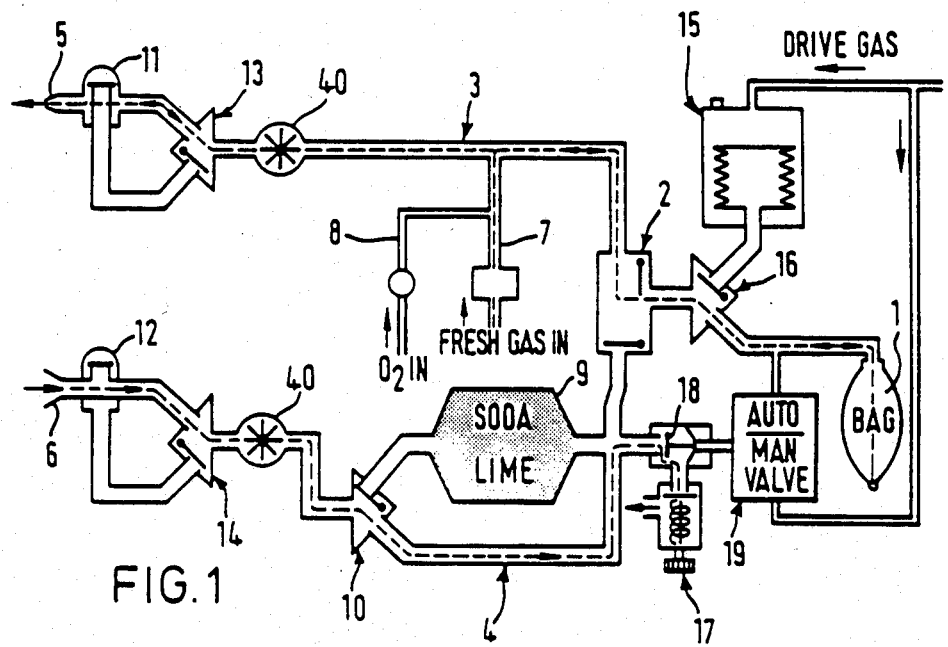
FIG. 1 is a schematic diagram of one embodiment of apparatus in accordance with the invention.

Referring firstly to FIG. 1, the apparatus for controlling the supply of gases to and from a patient in an anaesthesia system comprises a reservoir bag 1, a selector valve 2 and first and second flow passages 3,4 terminating at patient connection ports 5,6. The ports 5,6 may be connected by flexible plastic or rubber hoses of suitable length to a Y-piece (not shown), the third limb of the Y forming the connection port to the lungs of the patient.

The first passage 3 includes a fresh gas inlet 7 which in use is connected to a source of anaesthetic gases, for example, a mixture of nitrous oxide, oxygen and anaesthetic vapour. In addition, a line 8 is provided which is connected to a source of oxygen. The oxygen may be used initially to flush the apparatus, or alternatively may be used in an emergency to resuscitate a patient. The second flow passage 4 includes a soda-lime filter 9 which may selectively be bypassed depending upon the setting of a valve 10. In addition, both passages 3, 4 include one-way valves 11,12 adjacent the ports 5,6. The one-way valves may or may not be operative depending on the condition of the adjacent valves 13,14 as will be described in more detail below.

The apparatus additionally comprises a mechanical ventilator 15 which may be connected to the selector valve 2 in preference to the reservoir bag 1 by means of a switching valve 16. The selector valve 2 is actuable to connect either or both of the flow passages 3,4 to the switching valve and thus to the bag 1 or to the ventilator 15.

A spill valve 17 communicates with the second flow passage 4 and includes a pressure sensitive sealing member 18 which may be connected by means of a valve 19 either to the outlet from the bag 1 or to the drive gas circuit for the mechanical ventilator 15.

Figure 2:
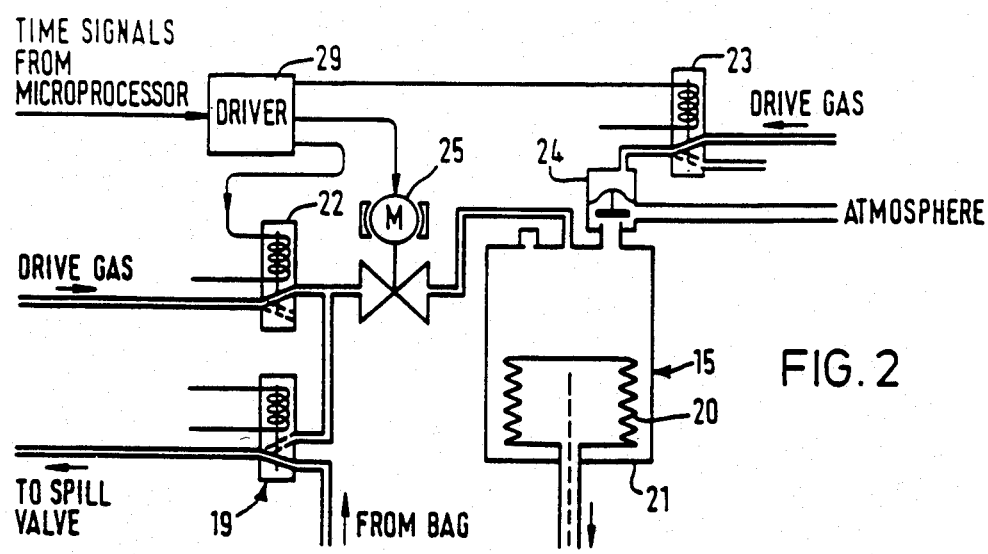
FIG. 2 is a schematic view of the mechanical ventilator drive circuit.

As shown schematically in FIG. 2, the mechanical ventilator 15 includes compressable bellows 20 mounted in a rigid chamber 21. The chamber 21 can be pressurized and opened to atmosphere in a cyclical manner by means of electronically controlled valves 22,23, the valve 22 controlling the inlet of the pressurizing drive gas and the valve 23 controlling the drive gas supply to a pressure sensitive release valve 24.

A stepper motor 25 controls the rate of flow of the drive gas into the chamber 21. The motor 25 and the valves 22,23 are responsive to control means of the apparatus, described in more detail below, such that when mechanical ventilation is used, the breathing frequency may be selected and accurately regulated.

Figure 3:
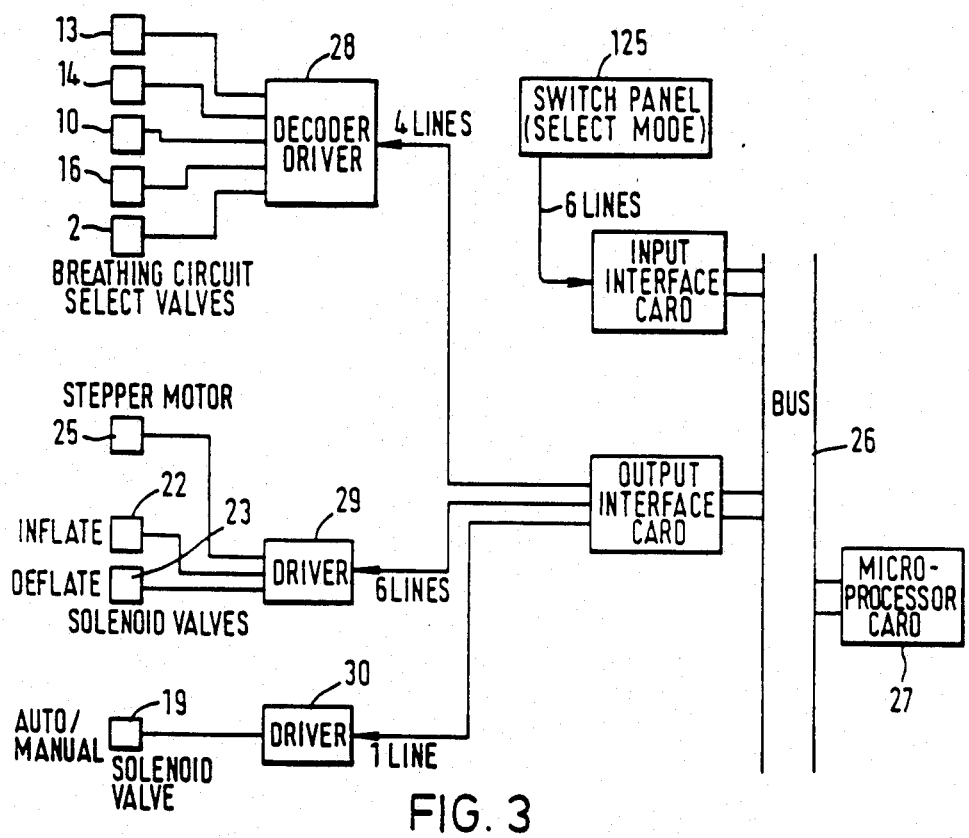
FIG. 3 is a block diagram of the control circuitry.

Turning now to FIG. 3, electronic control means for the apparatus shown in FIG. 1 are schematically illustrated. A switch panel 25 enables the operator to select one of a number of possible modes of operation, the signals from the switch panel being input into a microprocessor 27 via a bus 26. The microprocessor is pre-programmed such that, in response to a particular mode selected by the operator, output signals are applied to drivers 28,29,30. These in turn actuate the various valves of the apparatus in accordance with the selected mode, as will be explained in more detail below.

The valves 2, 10, 13, 14, 16 are illustrated schematically only in FIG. 1 for the purposes of describing the various modes of operation of the system. It will be appreciated that the valves should be so constructed as to be responsive to the control signals from the microprocessor to provide the required switching between the different operational configuration discussed below. Such valves may conveniently be solenoid controlled. Furthermore, the valves of the apparatus preferably include sensing means (not shown), for example Hall Effect sensors, adapted to provide a signal indicative of the condition of the respective valves, so that the microprocessor may monitor the state of each valve and provide an emergency signal in the event of valve failure.

Referring now to FIG. 1, the various modes of operation of the system will be described.

In FIG. 1, the valves are set by the microprocessor such that the configuration corresponds to a Mapleson A gas supply system. Thus, the selector valve 2 and the switching valve 16 are set such that the reservoir bag 1 is connected to the flow passage 3 and is shut off from the flow passage 4. The valves 13,14 are set such that the one-way valves 11,12 are effectively bypassed, and the valve 10 is effective to bypass the soda-lime filter. In this mode of operation, which is particularly suited for use with a patient who breathes spontaneously, the reservoir bag stores fresh gas, which enters at a constant flow rate via the inlet 7 during the expiratory phase. During inspiration the patient inhales gas from the bag at a rate much greater than the continuous fresh gas flow rate. Excess expired gas is vented from the system via the spill valve 17. In this mode, there is limited rebreathing, since the fresh gas entering via the inlet 7 swamps the exhaled gases during filling of the bag 1, and because the volume of the expiratory limb (in this mode the flow passage 4) is limited. Flow meters 40 are provided in both passages 3,4 so that the microprocessor may monitor the volume of gas passing to and from the patient.

Figure 4:
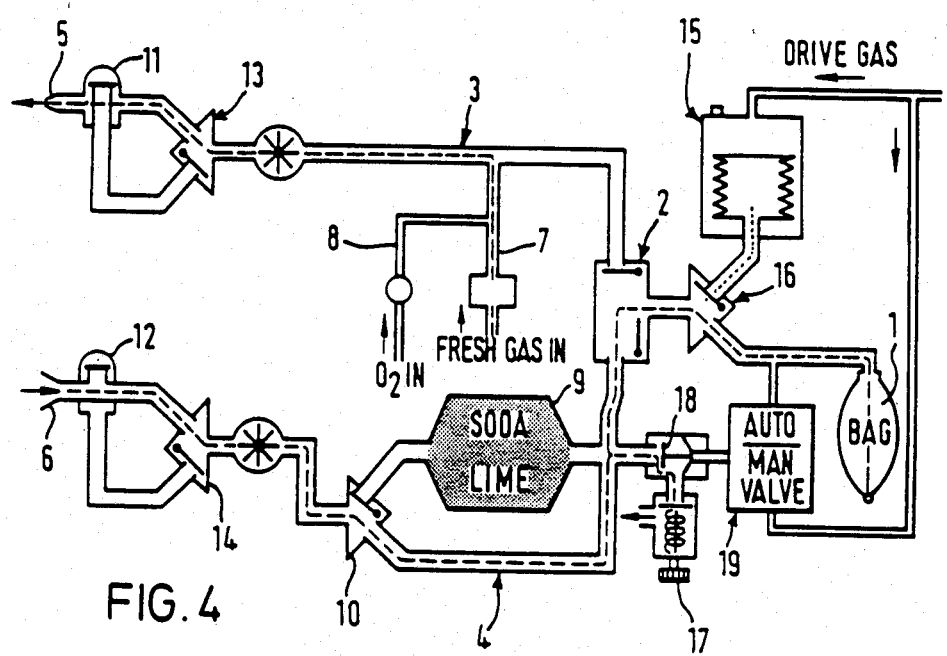
FIGS. 4, 5 and 6 illustrate the apparatus shown in FIG. 1 in different modes of operation.

FIG. 4 illustrates a second mode of operation of the apparatus equivalent to a Mapleson D gas supply system. In this mode of operation, the control means actuates the selector valve 2 such that the port leading to the first flow passage 3 is closed off, and that leading to the second flow passage is opened connecting the bag 1 to the second flow passage 4. Thus, the bag 1 has effectively been transferred to the expiratory limb, and fresh gas is delivered to the patient through a low compliance, small volume inspiratory limb (the closed flow passage 3). Lung ventilation is produced by a displacement of exhaled gas to and from the bag 1, with an escape of gas from the spill valve 17 during exhalation being equal in volume to the fresh gas flow. As such, in this mode of operation there is considerable rebreathing by the patient of exhaled gas. In the mode of operation shown in FIG. 4, the physician may be required manually to ventilate the patient by squeezing the bag 1, so as to force gas into the patient's lungs. In this event, a manual mode switch is depressed on the control panel and the microprocessor actuates the valve 19, such that the spill valve closure member 18 is in flow communication with the bag outlet. In this way, as the physician squeezes the bag the resulting increase in the pressure causes the spill valve to be shut so that gases cannot escape via the spill valve during inflation of the lungs.

The mode of operation illustrated in FIG. 4 is also suitable for automatic ventilation by means of the mechanical ventilator 15. If this mode is desired, the appropriate switch is depressed on the control panel and the microprocessor then causes the switching valve 16 to change state such that the port leading to the ventilator is opened and the port leading the to the bag is shut. In this mode, the microprocessor also causes the valve 19 to switch over so that the pressure sensitive closure member of the spill valve is in flow communication with the drive gas inlet of the mechanical ventilator. Thus, when the drive gas is forced into the ventilation chamber so as to compress the bellows and inflate the patient's lungs, the increase in pressure causes the spill valve closure member 18 to remain in the closed condition. In the automatic mode, the driver 29 in response to the signals from the microprocessor is also effective to actuate the drive gas control valves 22,23 and the stepper motor 25 so that the frequency of the ventilator is accurately regulated.

Figure 5:
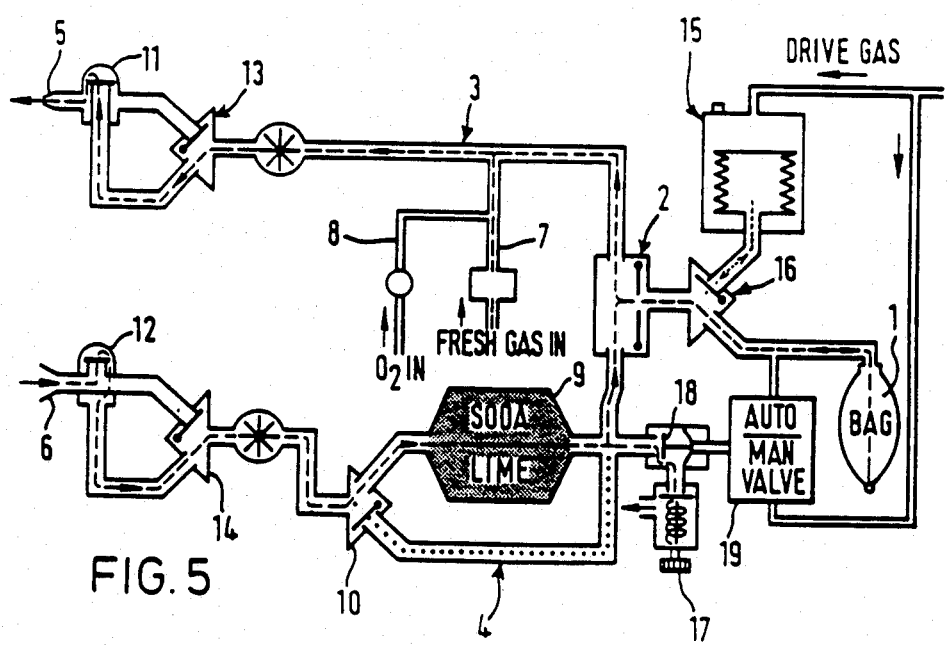

Referring now to FIG. 5, a third mode of operation is illustrated corresponding to a circle system. In this mode of operation, the valves 13,14 are switched over so that the flow of gas is directed through the one-way valves 11,12. Thus, in this mode gases can only enter the patient's lungs via the flow passage 3 and can only leave the patient via the flow passage 4. In this mode of operation the selector valve 2 is actuated such that all the ports thereof are open and the bag 1 is thus connected to both limbs of the apparatus. This system permits considerable rebreathing, since gases are recirculated to and from the patient. Accordingly the valve 10 is generally switched over in this mode, so that the gases are passed through the soda-lime filter whereby carbon dioxide will be absorbed before gas is rebreathed. With this configuration, the fresh gas flow may be related to metabolic requirements rather than to the required volume of the respired gas. It may be desirable to operate the system with the soda-lime filter bypassed, in which case a higher fresh gas flow is required. As in the mode of operation illustrated in FIG. 4, the circle system may alternatively be used for mechanical ventilation. In this case the automatic mode switch is depressed such that the microprocessor appropriately actuates the valves 16 and 19 as discussed above.

Figure 6:
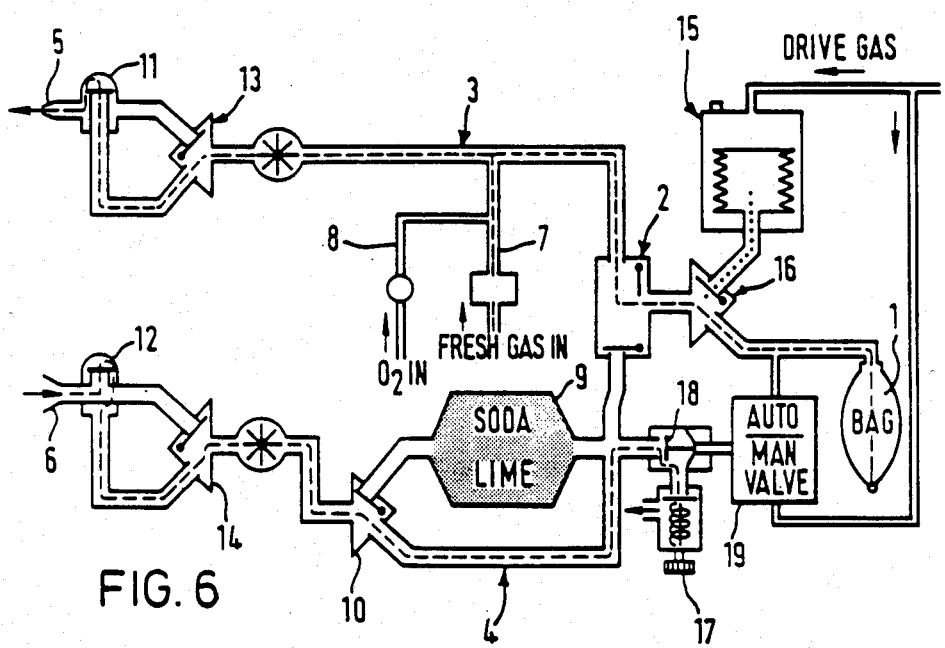

Finally, FIG. 6 illustrates a fourth mode of operation which permits no rebreathing whatsoever. In this mode, the bag 1, or the ventilator 15, is again connected to the first passage 3, the selector valve 2 being shut off from the passage 4. As in the FIG. 7 mode, the valves 13,14 are set such that the one-way valves 11' and 12' are operative. It will be seen that in this mode with no flow communication between the passages 3,4, the one-way valves are effective to prevent rebreathing. This mode of operation is particularly suited to the use of air rather than oxygen-rich mixtures and can be used either for spontaneous or mechanical ventilation.

It will be seen that the apparatus in accordance with the inventin enables different modes of operation to be selected quickly without the need to change hose connections. The microprocessor is programmed such that only desired combinations of the valve settings may be selected avoiding potentially dangerous configurations.

It will be appreciated that the specific arrangement of valves described by way of example above may be varied. For example, instead of a single selector valve 2, separate valves may be provided for each flow passage, which may be actuable independently of one another in order to connect the the switching valve to either or both flow passages 3, 4. Furthermore, in an alternative arrangement, the valves 13, 14, which are effective to bypass the one-way valves 11, 12 may be omitted. Instead one-way valves may be provided adjacent to ports 5, 6, the operation of each being directly controlled by the microprocessor.

Figure 7:
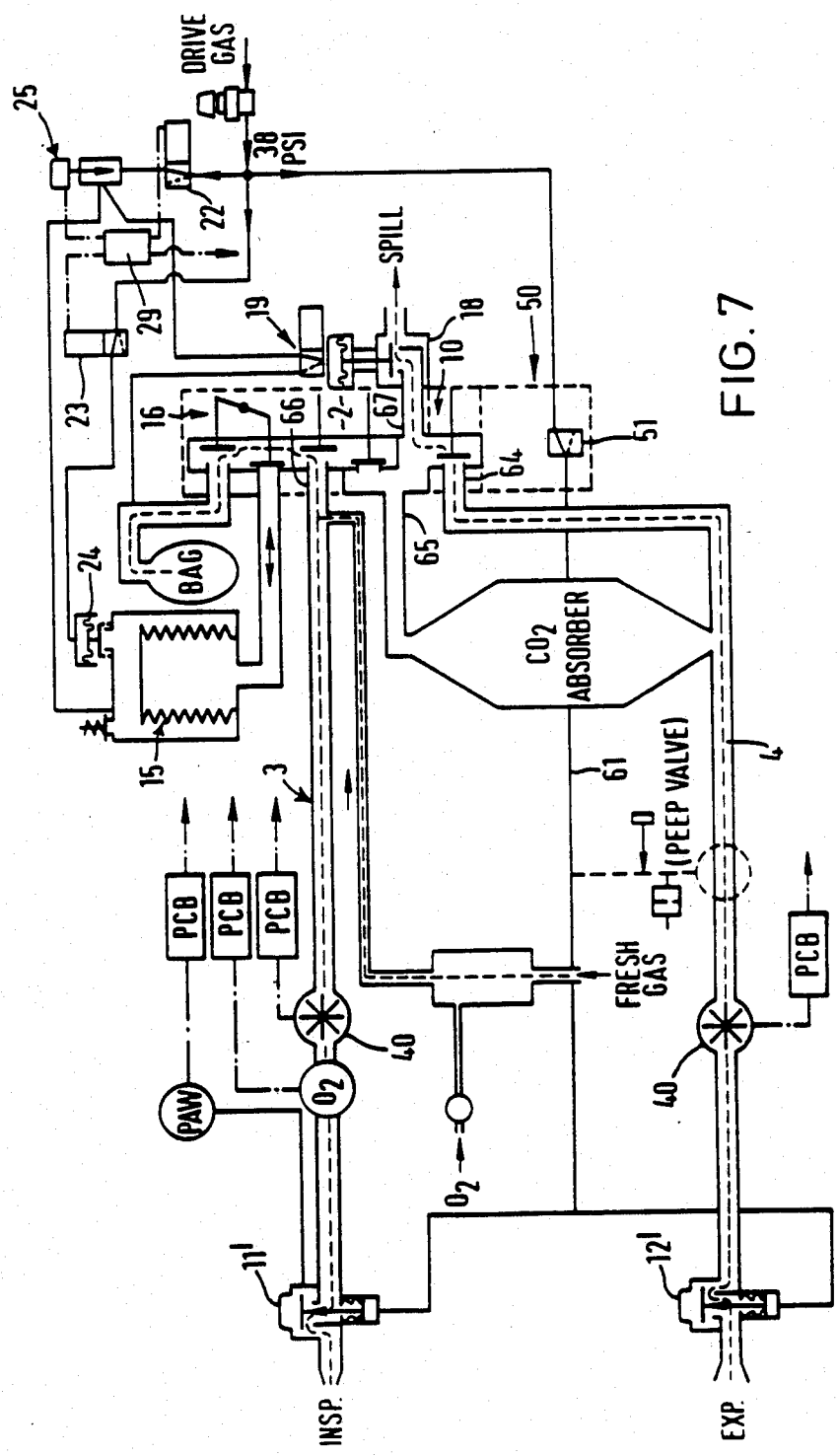
FIG. 7 is a schematic diagram of an alternative embodiment.

Turning now to FIG. 7 an alternative embodiment of the apparatus is illustrated wherein the selector valve 2, the switching valve 16 and the valve 10, for controlling whether or not the carbon dioxide filter is bypassed, are combined into a single unit 50, as is a valve 51, which controls whether or not the one-way valves 11,12 are operable, as will be described in greater detail below. The remaining components of the apparatus shown in FIG. 7 correspond generally to those shown in the FIG. 1 embodiment, and like reference numerals have been used to illustrate like components. Furthermore, the mechanical ventilator drive circuit illustrated in FIG. 7 corresponds to that shown in FIG. 2. It will be seen that, like the FIG. 2 arrangement, a solenoid controlled valve 19 is provided to communicate either the bag or the mechanical ventilator with the spill valve 18 to ensure that the spill valve is closed as gas is forced to the patient during controlled ventilation.

Figure 12:
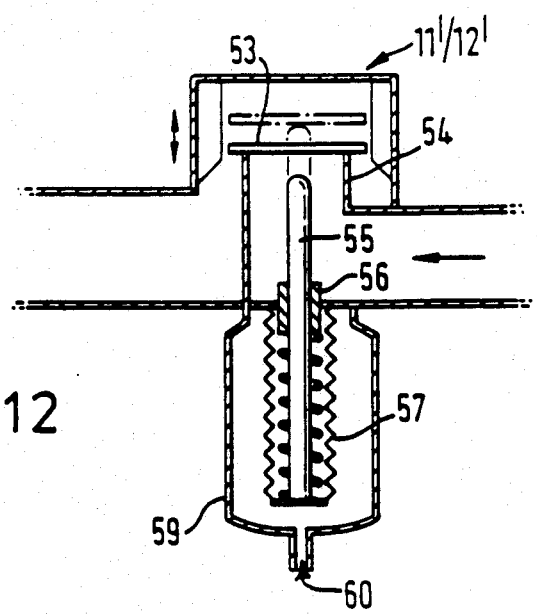
FIG. 12 is a schematic cross-sectional view of a one way valve.

Referring to FIG. 12, the details of the one-way valves 11', 12' provided in the flow passages 3,4 of the FIG. 7 embodiment are illustrated. It will be seen that each valve includes a rigid disc 53 which is guided with minimum friction so that it engages a horizontal valve seat 54 under the influence of gravity in the operational condition of the valve. In this condition, the passage of gas in the forward direction is permitted once the pressure is sufficient to overcome the weight of the disc, but reverse flow is prevented as gas pressure then increases the closing force on the disc. Means for rendering the one-way valve inoperable in are provided the form of a rod 55 guided through a sealed bearing 56 in the base of the valve and joined to a pressure responsive element 57 such as a spring loaded bellows. A sealed pressure vessel 59 encloses the element 57 so that a pressure applied to an inlet port 60 will compress the element 57 and raise the rod 55. As shown in broken lines, in the raised position of the rod 55, the disc 53 is unable to close on the seat 54, and therefore flow of gas through the valve in both directions is permitted. Pressure signals are applied to the inlets 60 of the valves 11', 12' via a line 61 (FIG. 7). Line 61 is connected to the supply of drive gas for the mechanical ventilator via a valve 51 forming part of the unit 50 described in more detail below.

Figure 8:
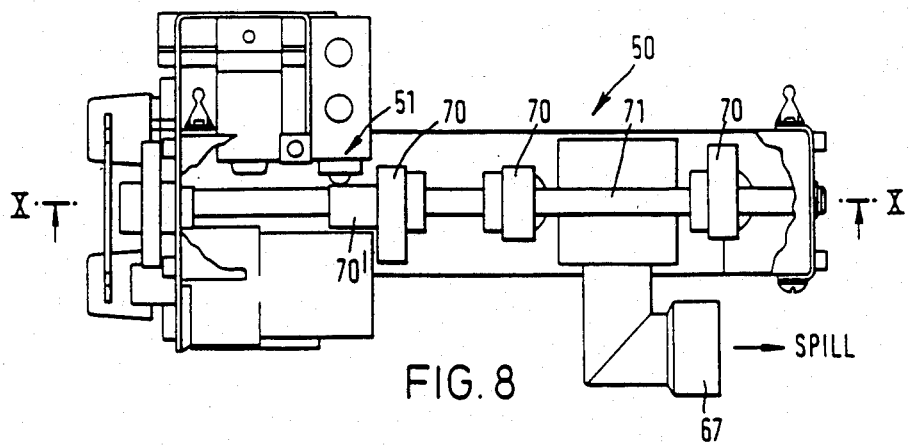
FIG. 8 is a side elevation of the valve unit for the embodiment shown schematically in FIG. 7.
Figure 10:
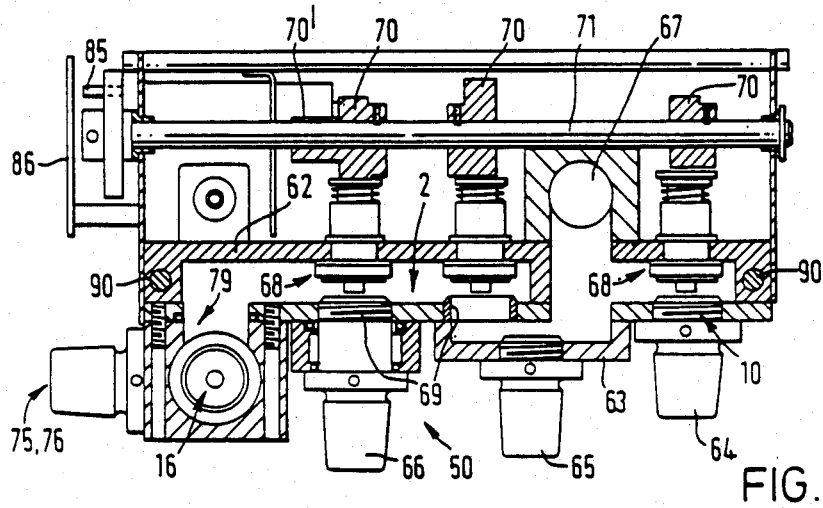
FIG. 10 is a cross section taken along line X—X in FIG. 8.
Figure 9:
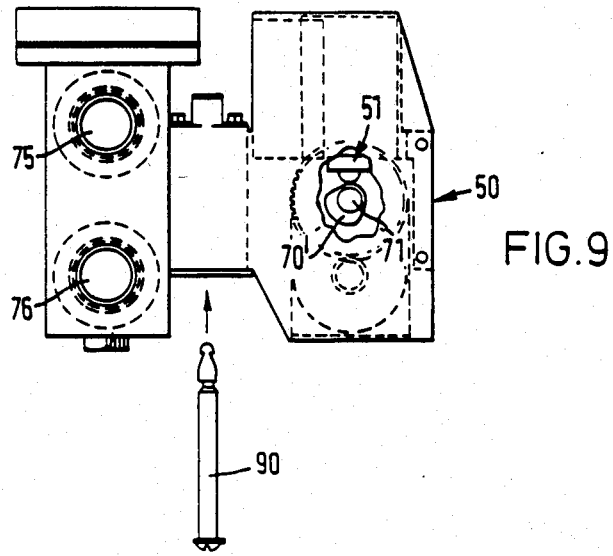
FIG. 9 is an end elevation of the unit shown in FIG. 8.

Turning to FIGS. 8 to 10, the details of the valve unit 50 are illustrated. The unit 50 comprises a block 62 secured to a cover plate 63 defining the valve chambers therebetween. The coverplate 63 includes a port 64 for connection to the second flow passage 4, a port 65 for connection to the carbon dioxide absorber, and a port 66 for connection to the first flow passage 3. A further port 67 is provided for connection to the spill valve 18.

The selector valve 2 comprises two poppet valve assemblies 68 arranged to be forced into sealing contact with respective valve seats 69 by means of cams 70 carried by a rotatable shaft 71. Similarly, valve 10 compises a poppet valve assembly 68 likewise operable by means of a cam 70 carried by shaft 71.

The unit 50 further comprises the actuating valve 51 (not shown in detail) for the one-way valves 11', 12'. Valve 51 is also actuable under the action of a cam 70' carried by the shaft 71. The unit 50 also mounts the switching valve 16. The valve 16 includes ports 75, 76 for connection respectively to the mechanical ventilator and the ventilating bag.

Figure 11:
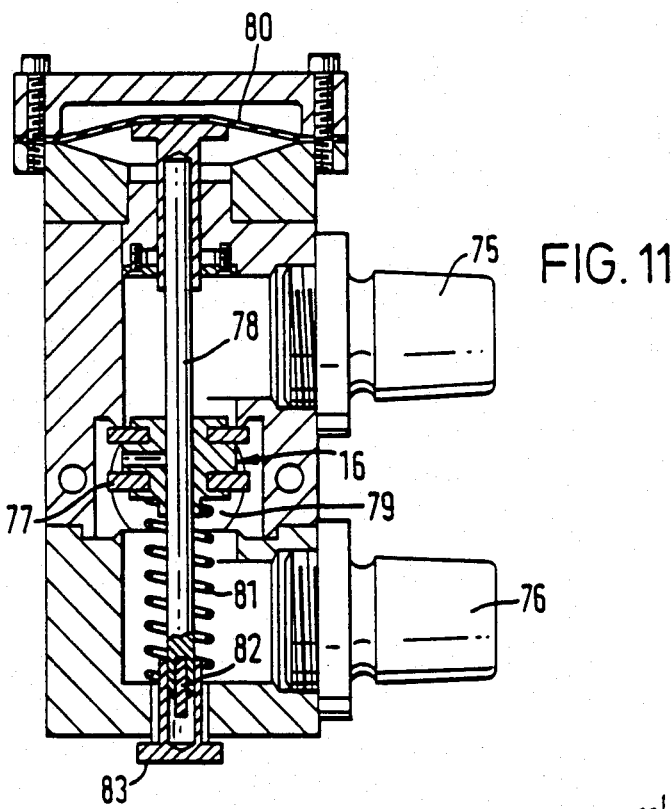
FIG. 11 is a cross-sectional view on an enlarged scale of the pneumatically operated switching valve incorporated in the unit shown in FIGS. 8 to 10.

The details of the switching valve 16 are shown in FIG. 11, from which it will be seen that the valve includes an axially moveable closure member 77 mounted on a shaft 78 moveable between a first position wherein inlet port 79 (FIG. 10) of the valve 16 communicates with the port 76 connected to the bag, and a second position wherein the inlet 79 communicates with the port 75 connected to the mechanical ventilator. the valve 16 is actuated into the second position by the application of a pneumatic signal on a diaphragm 80 engaging the upper end of the shaft 78. The pneumatic signal may conveniently be supplied automatically upon switching of the solenoid valve 19 into the condition wherein mechanical ventilation can occur. The valve 16 further comprises a biasing spring 81 arranged to urge the closure member 77 into its first condition when actuating pressure is removed from the diaphragm 80. In this way, in the event of electrical power or gas supply failure, the valve 16 is returned to the condition wherein the ventilator bag rather than the mechanical ventilator is connected to the patient. This is important from the safety point of view. The shaft 78 of the valve 16 is provided at one end with a magnet 82 arranged to operate a Hall Effect switch associated with an end cap 83 whereby the microprocessor may monitor the condition of the switching valve.

Referring once more to FIGS. 8 to 10, the shaft 71 carrying the actuating cams 70 can be rotated by means of a suitable motor (not shown) controlled by the microprocessor or alternatively can be adapted to be rotated by hand. A magnet 85 is mounted on an arm extending radially from one end of the cam shaft and is located adjacent a printed circuit board 86 which carries a series of Hall Effect switches arranged so that the rotational position of the cam shaft can be encoded electrically and thus monitored by the microprocessor. (It will be noted that the printed circuit board and magnet have been removed from FIG. 9 which is partly broken away to illustrate the cam 70' which engages the actuating valve 51 for the one-way valves 11',12').

It will be seen that rotation of the cam shaft 71 is effective to control the operation of valves, 2, 10, 51 and thus 11',12' simultaneously. The operational sequence of the valves is illustrated in FIGS. 13a to 13d. Referring first to FIG. 13d, in a first angular position of the cam shaft 71 the valve 10 is open, while the selector valve 2 is set so that the inlet port 79 of the switching valve is connected to the flow passage 3. Furthermore, the actuating valve 51 is actuated so that a pneumatic signal is applied to one-way valves 11',12' whereby such valves are inoperable and permit bidirectional flow. This mode of operation is illustrated schematically in FIG. 7. It will be seen that the configuration is a Mapleson A configuration corresponding to that illustrated in FIG. 1. Accordingly, in this configuration, the switching valve 16 is maintained in its first position wherein the inlet port thereof and thus the first flow passage 3 is connected to the ventilator bag.

Figure 14:
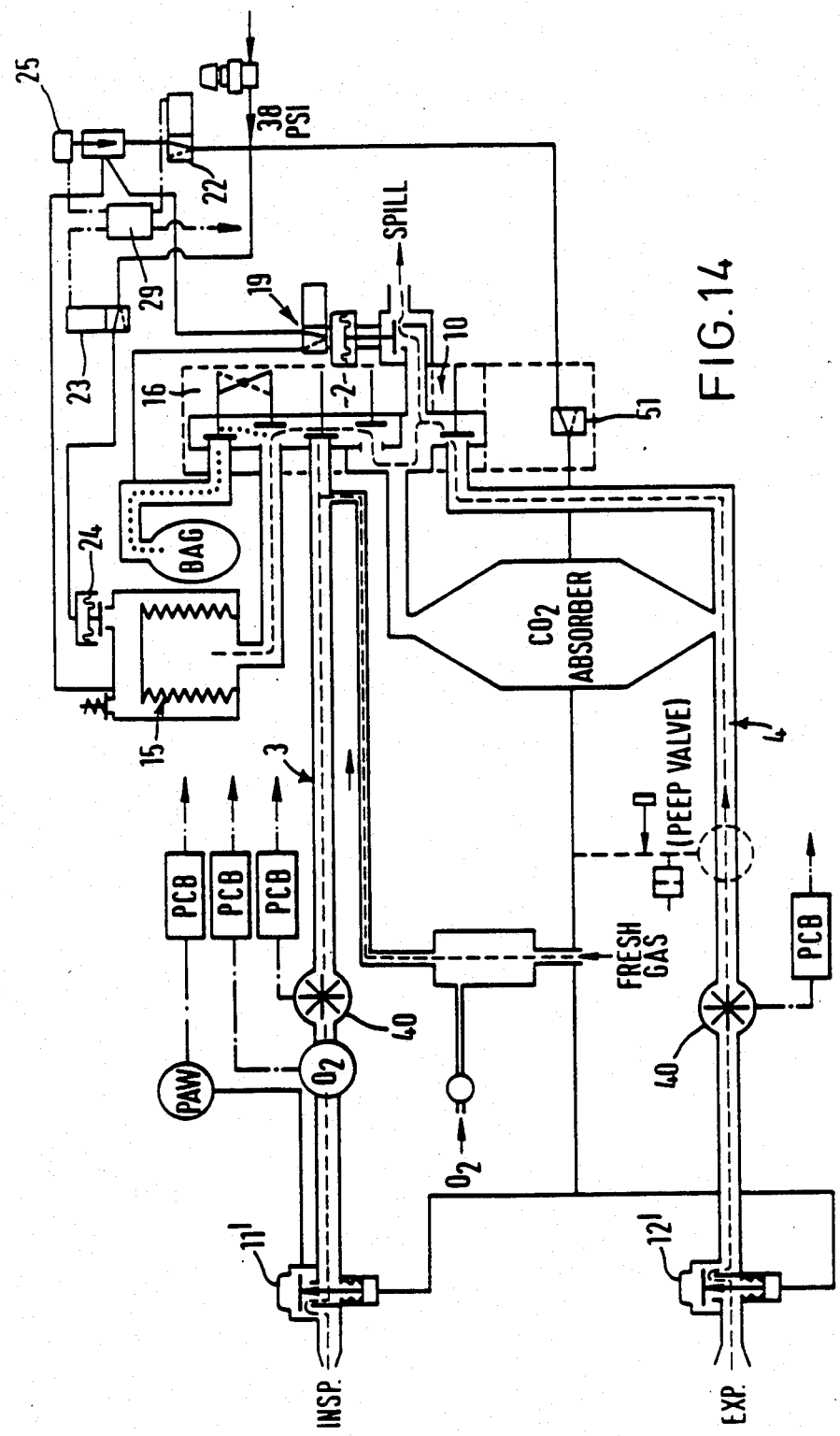
FIGS. 14 and 15 illustrate the apparatus shown in FIG. 7 in different modes of operation.

As shown in FIG. 13c, rotation of the cam shaft through 90° from the position shown in FIG. 13d is effective to reverse the setting of the selector valve 2 such that, as shown in FIG. 14, the second flow passage 4 is connected to the inlet port of the selector valve 16. The settings of the valves 10 and 51 are, however, not altered. It will therefore be seen that this configuration is a Mapleson D configuration corresponding to that illustrated in FIG. 4. Accordingly, the switching valve 16 may be set in either of its positions, depending on whether or not mechanical ventilation is required.

Figure 15:
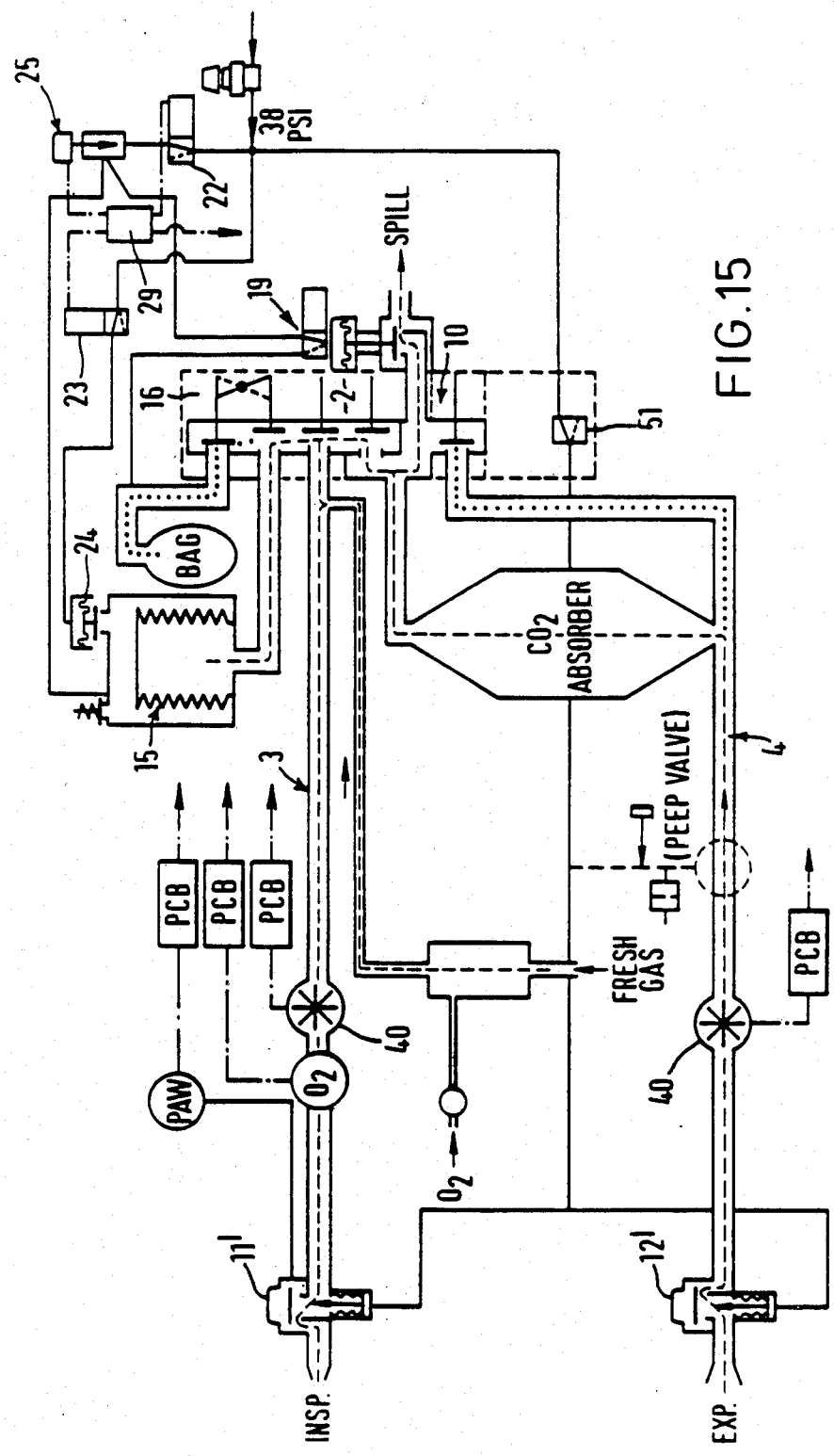

FIGS. 13a and 13b illustrate the configurations of the valve unit 50 providing a circle system as shown in FIG. 15. In this configuration, which corresponds to that illustrated in FIG. 5, both the poppet valve assemblies of the selector valve 2 are open, so that the inlet to the switching valve is connected to both of the flow passages 3, 4. In addition, the valve 51 is moved to a closed condition, such that a pneumatic signal is no longer supplied to the one-way valves 11',12' and these valves are operable accordingly. It will be seen that there are two angular positions of the cam shaft wherein the apparatus is set to a circle configuration. In the first shown in FIG. 13a, the valve 10 is closed, so that gases passing through the second flow passage 4 are forced through the port 65 of the unit 50 and thus through the carbon dioxide absorber. In the second condition shown in FIG. 13b, the valve 10 is opened (the remaining valve settings remaining unaltered) so that gases from the second flow passage may enter the unit 50 via the port 64 and the carbon dioxide absorber is thus bypassed. As discussed above, the circle system is suitable for use either with the mechanical ventilator or with the ventilator bag, and accordingly the switching valve 16 may be set to either of its positions in this configuration.

It will be appreciated that with the valve unit shown in FIGS. 8 to 10, undesirable configurations are avoided, since the cams on the cam shaft are shaped such that only the four illustrated configurations may be selected. A further advantage of this embodiment is that the unit 50 is relatively easy to dismantle for sterilization. In order to sterilize those parts of the unit in contact with expelled breath of the patient, heat or chemical treatment is employed. It is therefore necessary to separate the cam shaft and associated electrical components from the parts requiring sterilization. As shown in FIG. 9, this may readily be achieved by removing pins 90 which secure the cam shaft and associated components to the valve block 62.

We claim:

1. Apparatus for controlling the flow of gas to or from a patient in an anaesthesia system, said apparatus comprising a reservoir bag, a selector valve means operable in a first condition to connect said bag to said first flow passage, in a second condition to connect said bag to said second flow passage, and in a third condition to connect said bag to both of said first and second flow passages, said first and second flow passages being arranged in parallel and each being adapted to be connected at the end thereof remote from the selector valve means to a patient, said first passage comprising first one-way valve means selectively operable to prevent the back-flow of gas into said passage from the patient and communicating with an inlet for the supply of fresh gas, and said second flow passage comprising second one-way valve means selectively operable to prevent the flow of gas from said second flow passage to the patient and a selectively bypassable carbon dioxide absorbing means, there being a spill valve arranged to release gases from the second flow passage, wherein means are provided to control said conditions of the selector valve means and the selective operation of said first and second one-way valve means whereby desired modes of operation of the apparatus may be selected.

2. Apparatus as claimed in claim 1 further comprising a mechanical ventilator and switching valve means actuable to connect either the ventilator or the reservoir bag to the selector valve means.

3. Apparatus as claimed in claim 2 wherein the apparatus is arranged to be supplied from a power supply, and the switching valve is operable to connect the reservoir bag to the patient in the event of a break in the power supply to the apparatus.

4. Apparatus as claimed in claim 2 wherein means are provided to prevent opening of the spill valve in synchronism with inhalation during mechanical or manually controlled ventilation.

5. Apparatus as claimed in claim 4 wherein said spill valve includes a pressure sensitive closure member which is pressure communicable with a drive gas for the mechanical ventilator during mechanical ventilation and with an outlet from the reservoir bag during manually controlled ventilation.

6. Apparatus as claimed in claim 1 wherein the selector valve means comprises solenoid controlled closure members.

7. Apparatus as claimed in claim 1 further comprising a rotable shaft having a plurality of cam members, and wherein the selector valve means includes closure members which are mechanically controlled by said cam members.

8. Apparatus as claimed in claim 1 wherein the one-way valve means comprise gravity operated disc valves each having a valve closure disc.

9. Apparatus as claimed in claim 8 comprising selectively operable means for bypassing each one-way valve means.

10. Apparatus as claimed in claim 8 wherein each one-way valve means can be rendered inoperable by means of an element selectively actuable to maintain the valve closure disc in an open condition.

11. Apparatus as claimed in claim 1 further comprising means for sensing and monitoring the condition of the various valve means.

* * * * *